United States Patent
Shimada et al.

(10) Patent No.: US 8,359,906 B2
(45) Date of Patent: Jan. 29, 2013

(54) ENVIRONMENT TESTING APPARATUS CAPABLE OF CONTROLLING CONDENSATION AMOUNT, AND CONTROL METHOD THEREFOR

(75) Inventors: Tetsuya Shimada, Osaka (JP); Shinichirou Sakami, Osaka (JP); Kouki Sakane, Osaka (JP)

(73) Assignee: ESPEC Corp., Osaka (JP)

(*) Notice: Subject to any disclaimer, the term of this patent is extended or adjusted under 35 U.S.C. 154(b) by 167 days.

(21) Appl. No.: 13/055,053

(22) PCT Filed: Jun. 22, 2009

(86) PCT No.: PCT/JP2009/061320
§ 371 (c)(1),
(2), (4) Date: Jan. 20, 2011

(87) PCT Pub. No.: WO2010/010774
PCT Pub. Date: Jan. 28, 2010

(65) Prior Publication Data
US 2011/0126616 A1    Jun. 2, 2011

(30) Foreign Application Priority Data
Jul. 22, 2008   (JP) ................................ 2008-188876

(51) Int. Cl.
*G01N 25/62* (2006.01)
*G01N 5/02* (2006.01)
*G01N 25/56* (2006.01)

(52) U.S. Cl. ................................. 73/77; 73/73
(58) Field of Classification Search ................ 73/77, 73
See application file for complete search history.

(56) References Cited

U.S. PATENT DOCUMENTS

| | | | | |
|---|---|---|---|---|
| 5,318,361 A | * | 6/1994 | Chase et al. | 374/57 |
| 6,113,262 A | * | 9/2000 | Purola et al. | 374/45 |
| 2010/0040106 A1 | * | 2/2010 | Sakami | 374/28 |
| 2010/0127089 A1 | * | 5/2010 | Sakami | 236/44 C |

FOREIGN PATENT DOCUMENTS

| | | |
|---|---|---|
| JP | 62-19746 A | 1/1987 |
| JP | 7-27694 A | 1/1995 |
| JP | 10-078387 A | 3/1998 |
| JP | 10-78387 A | 3/1998 |

(Continued)

OTHER PUBLICATIONS

International Preliminary Report on Patentability issued in International Application No. PCT/JP2009/061320 dated Mar. 17, 2011 (6 pages).

(Continued)

*Primary Examiner* — Lisa Caputo
*Assistant Examiner* — Jamel Williams
(74) *Attorney, Agent, or Firm* — Osha Liang LLP (57) ABSTRACT

An object of the present invention is to provide an environment testing apparatus capable of achieving, on the surface of a test object, a stable condensation status with less variation in the condensation amount than that of already existing-art. The environment testing apparatus 100 includes a regulator 4. On the basis of a signal from a condensation amount sensor 9, the regulator 4 controls the temperature of a cooling/heating plate 6 between a deviation-added value of the wet bulb temperature obtained from the wet bulb 11, and a deviation-added value of the dew-point temperature inside the test chamber 1.

4 Claims, 8 Drawing Sheets

FOREIGN PATENT DOCUMENTS

| | | |
|---|---|---|
| JP | 3113823 B2 | 12/2000 |
| JP | 2004-340775 A | 12/2004 |
| JP | 2006-125076 A | 5/2006 |
| JP | 2007-271551 A | 10/2007 |

OTHER PUBLICATIONS

Abstract of JP62-0197461 (A), dated Jan. 28, 1987, supplied from the espacenet Worldwide database, 1 page.

Abstract of JP10-078387 (A), dated Mar. 24, 1998, supplied from the espacenet Worldwide database, 1 page.

Abstract of JP7-027694 (A), dated Jan. 31, 1995, supplied from the espacenet Worldwide database, 1 page.

Abstract of JP2007-271551 (A), dated Oct. 18, 2007, supplied from the espacenet Worldwide database, 1 page.

Abstract of JP2004-340775 (A), dated Dec. 2, 2004, supplied from the espacenet Worldwide database, 1 page.

Abstract of JP2006-125076 (A), dated May 18, 2006, supplied from the espacenet Worldwide database, 1 page.

International Search Report issued in PCT/JP2009/061320, mailed on Jul. 28, 2009, w/translation, 4 pages.

Office Action issued in corresponding Chinese Application No. 200980128148.0 dated Aug. 14, 2012, with English translation thereof (14 pages).

Patent Abstracts of Japan, Publication No. 10-078387, Published on Mar. 24, 1998, 1 page.

* cited by examiner

UPPER LIMIT TEMPERATURE
= WET BULB TEMPERATURE +A°C
(E.G., 20.9°C)

LOWER TEMPERATURE
=DEW-POINT TEMPERATURE -B°C
(E.G., 10.9°C)

(b)

UPPER LIMIT TEMPERATURE
= WET BULB TEMPERATURE +A°C
(E.G., 20.9°C)

LOWER TEMPERATURE
=DEW-POINT TEMPERATURE -B°C
(E.G., 10.9°C)

(c)

UPPER LIMIT TEMPERATURE
= WET BULB TEMPERATURE +A°C
(E.G., 20.9°C)

WET BULB TEMPERATURE
(E.G., 17.9°C)

LOWER TEMPERATURE
=DEW-POINT TEMPERATURE -B°C
(E.G., 10.9°C)

ENVIRONMENT TESTING APPARATUS CAPABLE OF CONTROLLING CONDENSATION AMOUNT, AND CONTROL METHOD THEREFOR

TECHNICAL FIELD

The present invention relates to an environment testing apparatus capable of controlling the condensation amount of a test object. Such an environment testing apparatus is for use in an electric insulation test of test objects such as electronic components and electronic materials.

BACKGROUND ART

Electronic devices having electronic components and electronic materials in recent years are used under various environments due to expansion of their use. For example, use of an electronic device under a highly humid environment may cause condensation in the electronic device. Due to this condensation, conductors may be shortcircuited, consequently leading to breakdown of the electronic device. For this reason, there has been an increasing demand for a suitably evaluation of the durability (electric insulation) of electronic devices against condensation.

For example, Patent Documents 1 and 2 each discloses an apparatus for conducting a condensation test. In the apparatus described in Patent Document 1, a seat for placing thereon a test piece is cooled to keep the temperature of the seat constant at a temperature nearby the dew-point temperature of the test chamber. This way, the apparatus maintains the condensation status of the test piece for a long time.

Further, in the apparatus of Patent Document 2, a condensation amount is determined based on an image of the surface of a test object taken by a TV imaging device, and a signal relative to the condensation amount is input to a cooler control unit. Then, the test object is cooled by a cooler to achieve a set condensation amount by the surface of the test object. Note that cooling of the test object is controlled by using the maximum cooling capability of the cooler.

PRIOR ART DOCUMENTS

Patent Document

Patent Document 1: Japanese Unexamined Patent Publication No. 19746/1987 (Tokukaishou 62-19746)
Patent Document 2: Japanese Unexamined Patent Publication No. 78387/1998 (Tokukaihei 10-78387)

SUMMARY

Technical Problem

However, with the apparatus of Patent Document 1, it is difficult to obtain an accurate condensation status. In other words, the apparatus enables rough control of the condensation amount, but not fine control of the condensation amount. Merely maintaining the temperature of the seat constant at a temperature nearby the dew-point temperature will not prevent variation in the condensation amount on the surface of the test piece over time.

The apparatus of Patent Document 2 on the other hand measures the condensation amount on the surface of the test object with a use of the TV imaging device. However, the apparatus of Patent Document 2 controls the condensation amount on the surface of the test object by utilizing as much as possible the cooling capability of the cooler. This enables a favorable response of the condensation amount towards a set condensation amount, but the condensation amount less likely converges at the set condensation amount. In other words, a stable condensation status with a small variation in the condensation amount is difficult to achieve.

The present invention is made in view of the above problems, and it is an object of the present invention to provide an environment testing apparatus capable of achieving a stable condensation status on the surface of a test object, with a small variation in the condensation amount.

Solution to Problem

As a result of deliberation to find the way to achieve the object, the inventors of the present invention provided a certain regulation to a controllable temperature range of a cooling/heating unit which cools and heats a test object. More specifically, a deviation-added value of a wet bulb temperature obtained by a wet bulb is set as the upper limit value of the controllable temperature range, and a deviation-added value of a dew-point temperature of a test chamber is set as the lower limit value. Then, the temperature of the cooling/heating unit is controlled within the controllable temperature range, based on signals from the condensation amount sensor, to control the condensation amount on the surface of the test object. This way variation in the condensation amount on the surface of the test object is kept less than variation taking place in a known-technology. Finding that this will achieve the above object, the inventors have completed the present invention.

A first aspect of the present invention is an environment testing apparatus, including: a test chamber into which a test object is placed; a wet bulb and a dry bulb disposed inside the test chamber, which obtain the temperature and the humidity of the air inside the test chamber; an air-conditioner which conditions the air inside the test chamber to predetermined temperature and humidity, based on signals from the wet bulb and the dry bulb; a cooling/heating unit accommodated inside the test chamber, which has a top surface for disposing thereon the test object and cools or heats the test object; a condensation amount sensor to be placed on the test object; and a controller which controls the condensation amount on the surface of the test object based on signals from the condensation amount sensor, by varying a temperature instruction value for the cooling/heating unit between a deviation-added value of a wet bulb temperature obtained by the wet bulb and a deviation-added value of a dew-point temperature of the test chamber.

The present invention is preferably adapted so that the controller controls the condensation amount on the surface of the test object by switching the temperature instruction value among one of the deviation-added value of the wet bulb temperature, a value of the temperature of the wet bulb, and the deviation-added value of the dew-point temperature.

The present invention is preferably adapted so that the controller controls the condensation amount on the surface of the test object by switching the temperature instruction value between the deviation-added value of the wet bulb temperature and the deviation-added value of the dew-point temperature.

A second aspect of the present invention is a method of controlling an environment testing apparatus including: a test chamber into which a test object is placed; a wet bulb and a dry bulb disposed inside the test chamber, which obtain the temperature and the humidity of the air inside the test chamber; an air-conditioner which conditions the air inside the test chamber to predetermined temperature and humidity, based on signals from the wet bulb and the dry bulb; a cooling/heating unit accommodated inside the test chamber, which has a top surface for disposing thereon the test object and cools or heats the test object; and a condensation amount sensor to be placed on the test object, the method including the steps of: conditioning the air inside the test chamber to predetermined temperature and humidity by operating the air-conditioner; measuring a condensation amount on the surface of the test object based on signals from the condensation amount sensor; and controlling the condensation amount on the surface of the test object so as to approximate the condensation amount to a predetermined amount, based on the condensation amount thus measured, by varying a temperature instruction value for the cooling/heating unit between a deviation-added value of a wet bulb temperature obtained by the wet bulb and a deviation-added value of a dew-point temperature of the test chamber.

Advantageous Effects of Invention

In the present invention, the condensation amount on the surface of a test object is controlled based on signals from the condensation amount sensor, by varying the temperature instruction value for the cooling/heating unit between a deviation-added value of a wet bulb temperature obtained by the wet bulb and a deviation-added value of a dew-point temperature of the test chamber. Thus, unnecessary increase/decrease in the temperature of the test object is restrained. Further, even if the temperature and the humidity inside the test chamber fluctuate to some extent, the temperature of the cooling/heating plate is controlled to handle the fluctuation (in other words, the condensation amount on the surface of the test object is controlled). As the result, it is possible to achieve a stable condensation status with less variation in the condensation amount.

DESCRIPTION OF EMBODIMENT

The following describes an embodiment of the present invention, with reference to the attached drawings.

(Structure of Environment Testing Apparatus)

Figure 1:
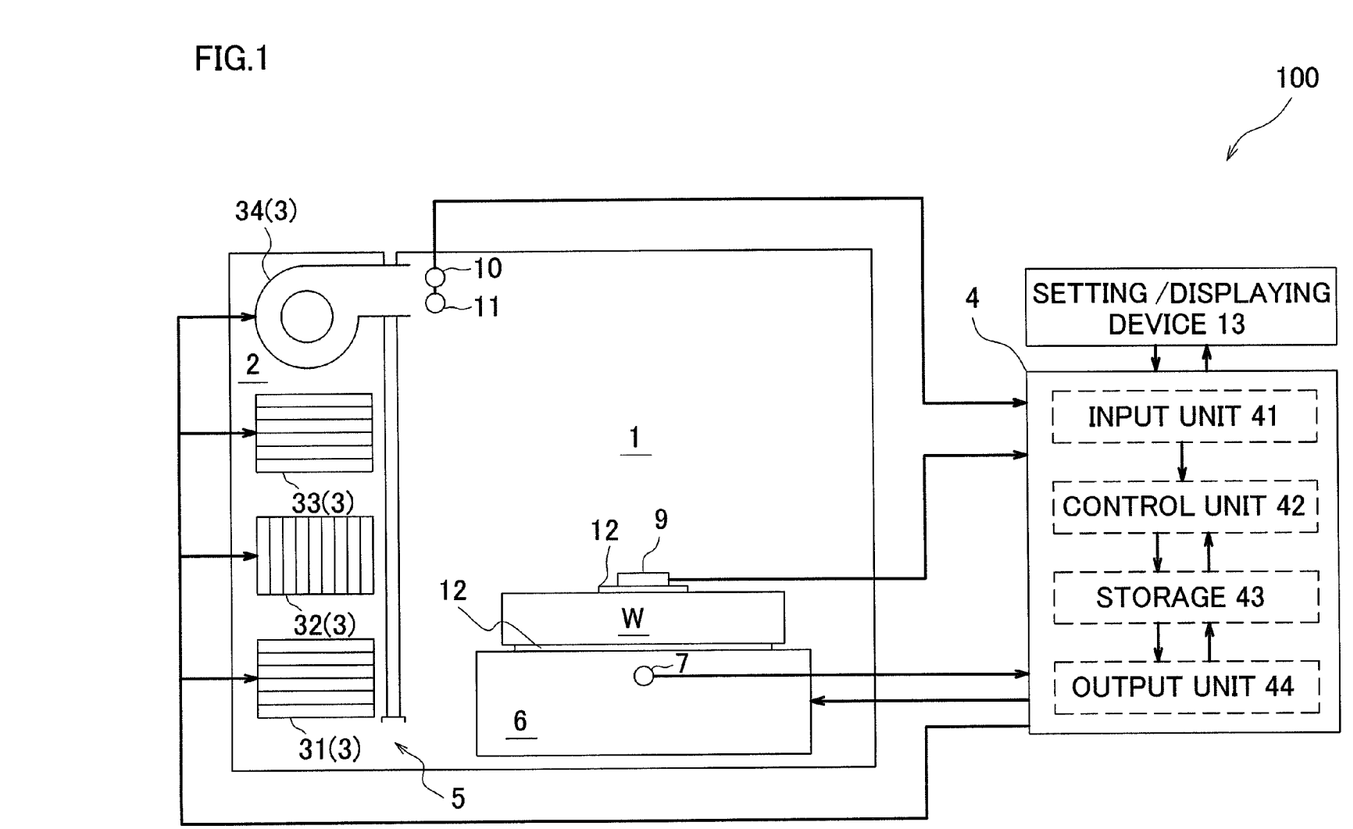
FIG. 1 shows a structure of an environment testing apparatus of one embodiment, according to the present invention.

FIG. 1 shows a structure of an environment testing apparatus 100 of an embodiment, according to the present invention. As shown in FIG. 1, the environment testing apparatus 100 includes: a test chamber 1 in which a test object W is placed; an air-conditioning room 2 which is parted from the test chamber 1; and a regulator 4 (controller). The test chamber 1 and the air-conditioning room 2 are parted from each other, except for a communicator 5 and an air blower 34 which circulate the air between the test chamber 1 and the air-conditioning room 2. In the test chamber 1 are disposed a dry bulb 10 and a wet bulb 11 each serving as a temperature/humidity sensor.

(Air-Conditioner)

In the air-conditioning room 2 is accommodated a heat/humidity generator 3 (air-conditioner) which conditions the air inside the test chamber 1 to predetermined temperature and humidity, based on signals from the wet bulb 11 and the dry bulb 10.

The heat/humidity generator 3 includes a humidifier 31 for humidifying the air to be supplied to the test chamber 1; a cooler 32 for cooling the air to be supplied to the test chamber 1; a heater 33 for heating the air to be supplied to the test chamber 1; and an air blower 34 for circulating the air between the test chamber 1 and the air-conditioning room 2. The air blower 34 communicates the upper space of the test chamber 1 with the air-conditioning room 2, and the communicator 5 communicates the lower space of the test chamber 1 with the air-conditioning room 2. The heat/humidity generator 3 conditions the temperature and the humidity of the air by the humidifier 31, the cooler 32, and the heater 33, and supplies the conditioned air to the test chamber 1 by the air blower 34, thus conditioning the air inside the test chamber 1 to predetermined temperature and humidity; e.g., 25° C. and 50% RH (Relative Humidity).

Note that the heat/humidity generator 3 does not necessarily have to be accommodated in the air-conditioning room 2 which is formed by parting a single casing into the test chamber 1 and the air-conditioning room 2 as in the present embodiment. The air-conditioner may be accommodated in an air-conditioning room 2 separated from the test chamber 1.

(Cooling/Heating Unit)

In the test chamber 1 is a cooling/heating plate 6 (cooling/heating unit) which cools and heats the test object W. The cooling/heating plate 6 is a surface-contacting cooling/heating unit having a cooling/heating surface which contacts the test object W to directly cool/heat the same by thermal conductance. Note that the test object W may be heated or cooled by indirect contact to the cooling/heating surface through a heat transfer sheet 12, instead of directly contacting the cooling/heating surface adopted in the present embodiment. The cooling/heating plate 6 may be a coolant-cooling type using a coolant such as a cold water, or a thermoelectric cooling type which is a combination of a thermoelectric element utilizing Peltier effect and a cooling fan.

The cooling/heating plate 6 also serves as a seat for placing thereon the test object W. On the top surface of the cooling/heating plate 6 is placed the test object W with a heat transfer sheet 12 interposed between the top surface and the test object W. Inside the cooling/heating plate 6 is mounted a first temperature sensor 7 for measuring the temperatures of the cooling/heating plate 6. In the present embodiment, the heat transfer sheet 12 is interposed between the cooling/heating surface of the cooling/heating plate 6 and the test object W, and the test object W is cooled or heated via the heat transfer sheet 12. Interposing the heat transfer sheet 12 improves the contact between the cooling/heating surface and the test object W.

This improves the thermal conductivity to the test object W. Further, on the top surface of the test object W is placed a condensation amount sensor with another heat transfer sheet 12 therebetween for improving the contact of the test object W to the condensation amount sensor 9.

The heat transfer sheet 12 is a sheet with excellent thermal conductivity and contact. Such a heat transfer sheet 12 may be, for example, a silicone rubber sheet, acrylic rubber sheet. The present embodiment adopts, as the heat transfer sheet 12, silicone-gel GR-b (Sarcon, manufactured by Fuji Polymer Industries Co., Ltd.).

(Condensation Amount Sensor)

Figure 2:
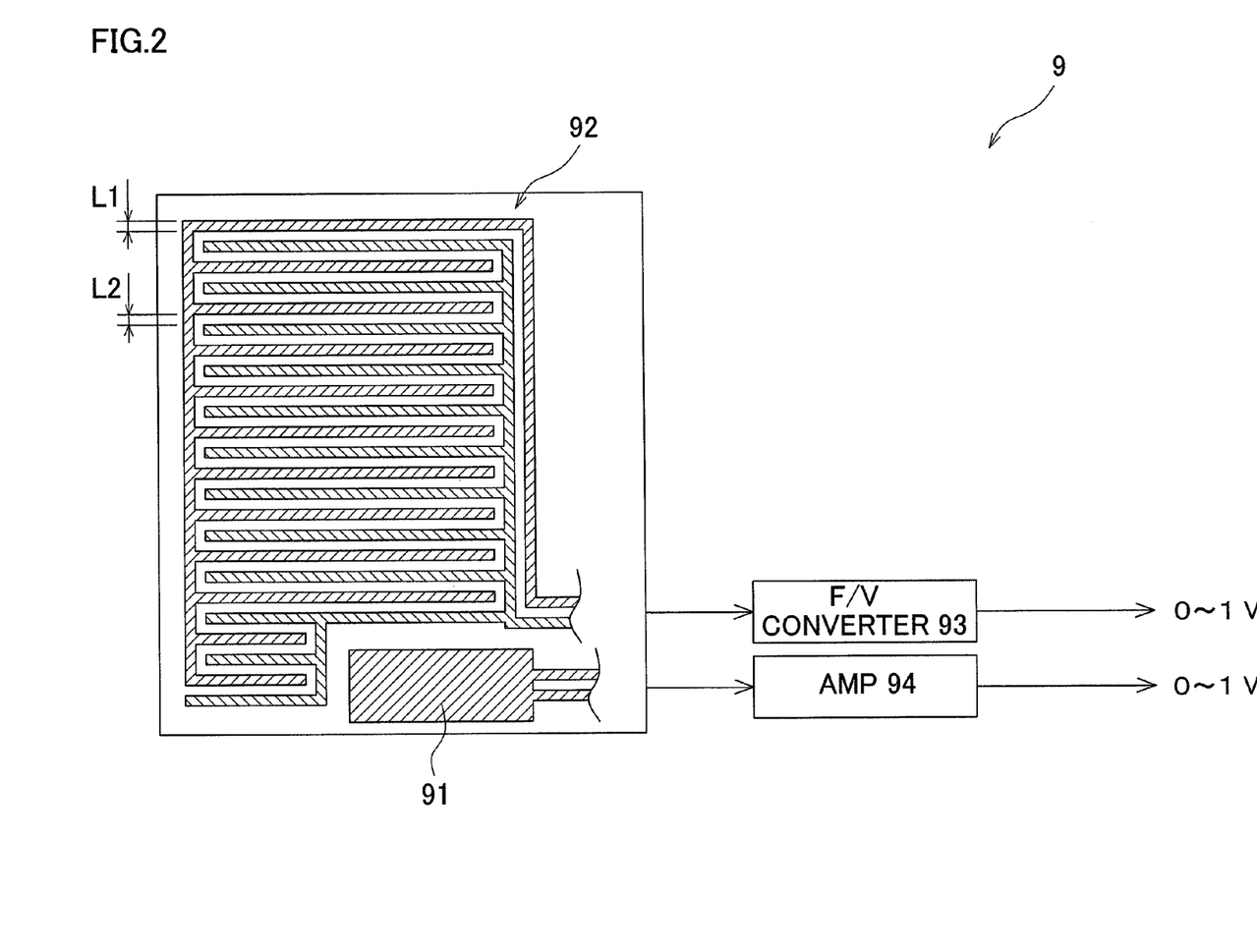
FIG. 2 provide detailed view of a condensation amount sensor shown in FIG. 1.

FIG. 2 provides a detailed view of the condensation amount sensor 9 shown in FIG. 1. As shown in FIG. 2, the condensation amount sensor 9 has a condensation sensor 92 and a second temperature sensor 91 which are disposed on a silicon wafer; a F/V converter 93 connected to the condensation sensor 92; and an AMP 94 connected to the second temperature sensor 91. The condensation sensor 92 has comb-shaped electrodes, and obtains the condensation amount on the condensation sensor 92, based on variation in the oscillating frequency corresponding to variation in the value of electrostatic capacity between electrodes. On the condensation sensor 92 is formed in microscopic wiring with the width L1 and the interval L2 of electrodes both being 30 μm. The F/V converter 93 is for performing a frequency-to-voltage conversion, and outputs signals ranging, for example, 0 to 1V, according to the condensation amount. Further, the second temperature sensor 91 uses, for example, a diode or thermistor, and is for obtaining the temperature of the sensor part of the condensation amount sensor 9. Note that a non-contact temperature sensor such as an infrared temperature sensor may be adopted in place of a diode or a thermistor. The AMP 94 is an amplifier for amplifying signals from the second temperature sensor 91.

The second temperature sensor 91 may be used for measuring the temperature of the test object W. It is preferable to incorporate signals from the second temperature sensor 91 into control, for the purpose of, for example, monitoring the status of the test object W. This way, it is possible to know whether the condensation amount sensor 9 is off the heat transfer sheet (or off the test object W). This is because when the condensation amount sensor 9 is off the heat transfer sheet 12 or off the test object W, the temperature obtained from the second temperature sensor 91 approximates the air temperature inside the test chamber 1 and does not follow the variation in the temperature of the cooling/heating plate 6 (i.e., variation in the signals from the first temperature sensor 7). It is further possible to know that the condensation amount sensor 9 is about to fall off from the heat transfer sheet 12 (or from the test object W), because hunting occurs in such a case in the signals from the second temperature sensor 91. Further, detection of an error in the first temperature sensor 7 is possible by comparing signals from the second temperature sensor 91 and the signals from the first temperature sensor 7. For example, if a temperature instruction value for the cooling/heating plate 6 does not match with the temperature obtained from the first temperature sensor 7, while the value substantially matches with the temperature obtained from the second temperature sensor 91, there is determined that an error has occurred in the first temperature sensor 7.

(Controller)

The environment testing apparatus 100 has a regulator 4 (controller) which controls the temperature and the humidity of the air inside the test chamber 1 and the temperature of the cooling/heating plate 6. The regulator 4 has an input unit 41, a control unit 42, a storage 43, and an output unit 44. Further, the regulator 4 is electrically connected to the dry bulb 10, the wet bulb 11, the condensation amount sensor 9, the heat/humidity generator 3, the cooling/heating plate 6, and the first temperature sensor 7. The regulator 4 receives signals from the dry bulb 10 and the wet bulb 11 via the input unit 41, and outputs instructions from the output unit 44 based on the received signals so as to control the heat/humidity generator 3 to condition the air inside the test chamber 1 to set temperature and humidity. Further, the regulator 4 receives via the input unit 41 signals from the dry bulb 10, the wet bulb 11, the condensation amount sensor 9, and the first temperature sensor 7 of the cooling/heating plate 6, and outputs instructions from the output unit 44 based on the received signals to control the cooling/heating plate 6 so that a set amount of condensation occurs on the surface of the test object W.

The regulator 4 is electrically connected to a setting/displaying device 13. The setting/displaying device 13 is for setting the temperature and the humidity of the air in the test chamber 1 and the condensation amount on the surface of the test object W, and for displaying the set values and measured values of the temperature and the humidity of the air in the test chamber 1, and the set value and measured value of the condensation amount on the surface of the test object W.

Figure 3:
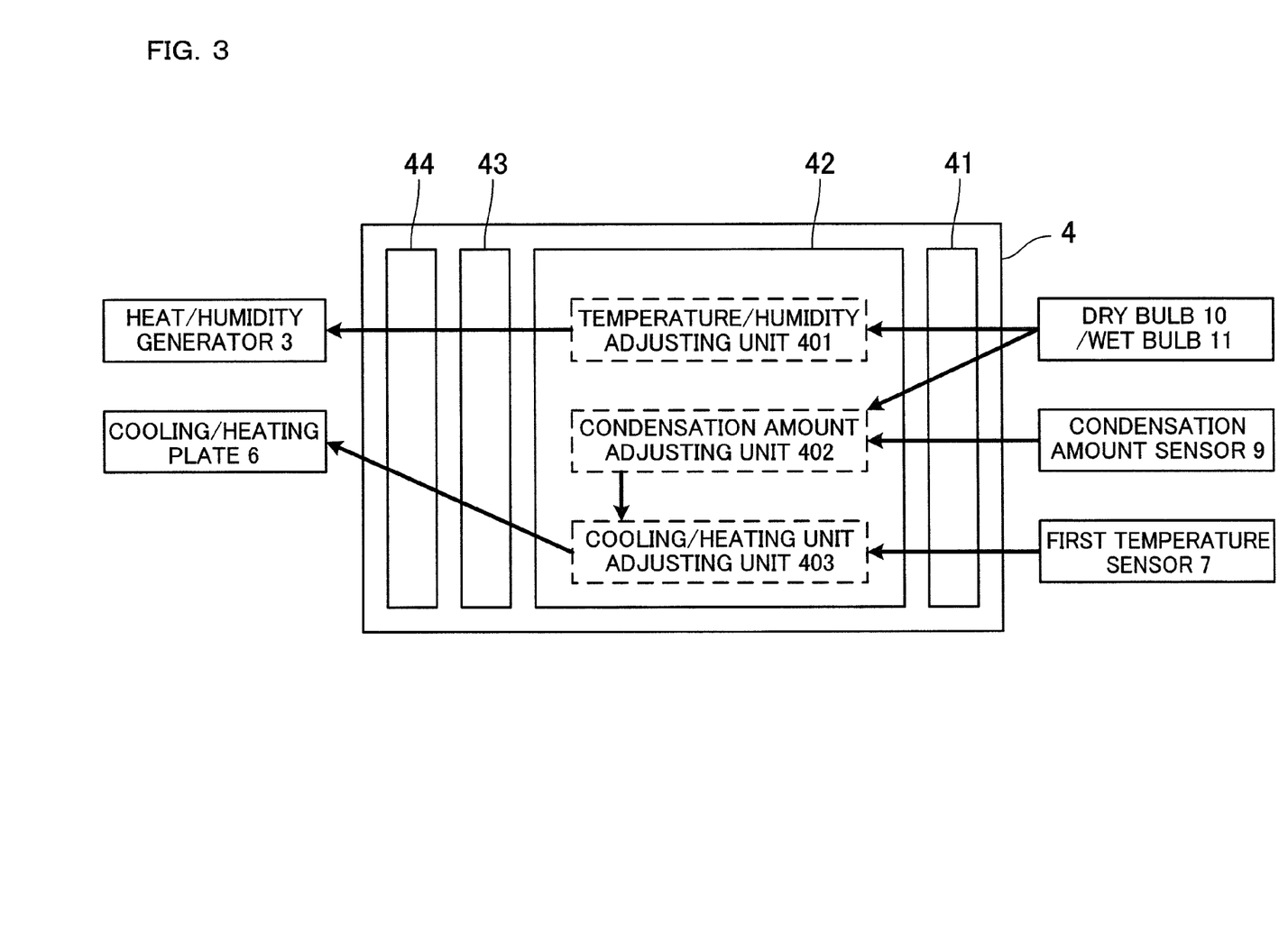
FIG. 3 is a block diagram showing details of a control unit of a regulator shown in FIG. 1.

FIG. 3 is a block diagram showing details of the control unit 42 of the regulator 4 shown in FIG. 1. The arrows in FIG. 3 show how signals flow. As shown in FIG. 3, the control unit includes a temperature/humidity adjusting unit 401, a condensation amount adjusting unit 402, and a cooling/heating unit adjusting unit 403.

The temperature/humidity adjusting unit 401 is an adjusting unit which determines an instruction value for the heat/humidity generator 3 based on signals from the dry bulb 10 and the wet bulb 11. The instruction value is output to the humidity generator 3 from the temperature/humidity adjusting unit 401, via the storage 43 and the output unit 44. The condensation amount adjusting unit 402 is an adjusting unit which determines the temperature instruction value for the cooling/heating plate 6, based on the signals from the dry bulb 10, the wet bulb 11, and the condensation amount sensor 9. The cooling/heating unit adjusting unit 403 outputs the temperature instruction value from the condensation amount adjusting unit 402 to the cooling/heating plate 6 via the storage 43 and the output unit 44, after comparing the temperature instruction value with a signal of the first temperature sensor 7 (actual temperature of the cooling/heating plate 6).

(Modification of Test Object W Fixing Method)

Figure 4:
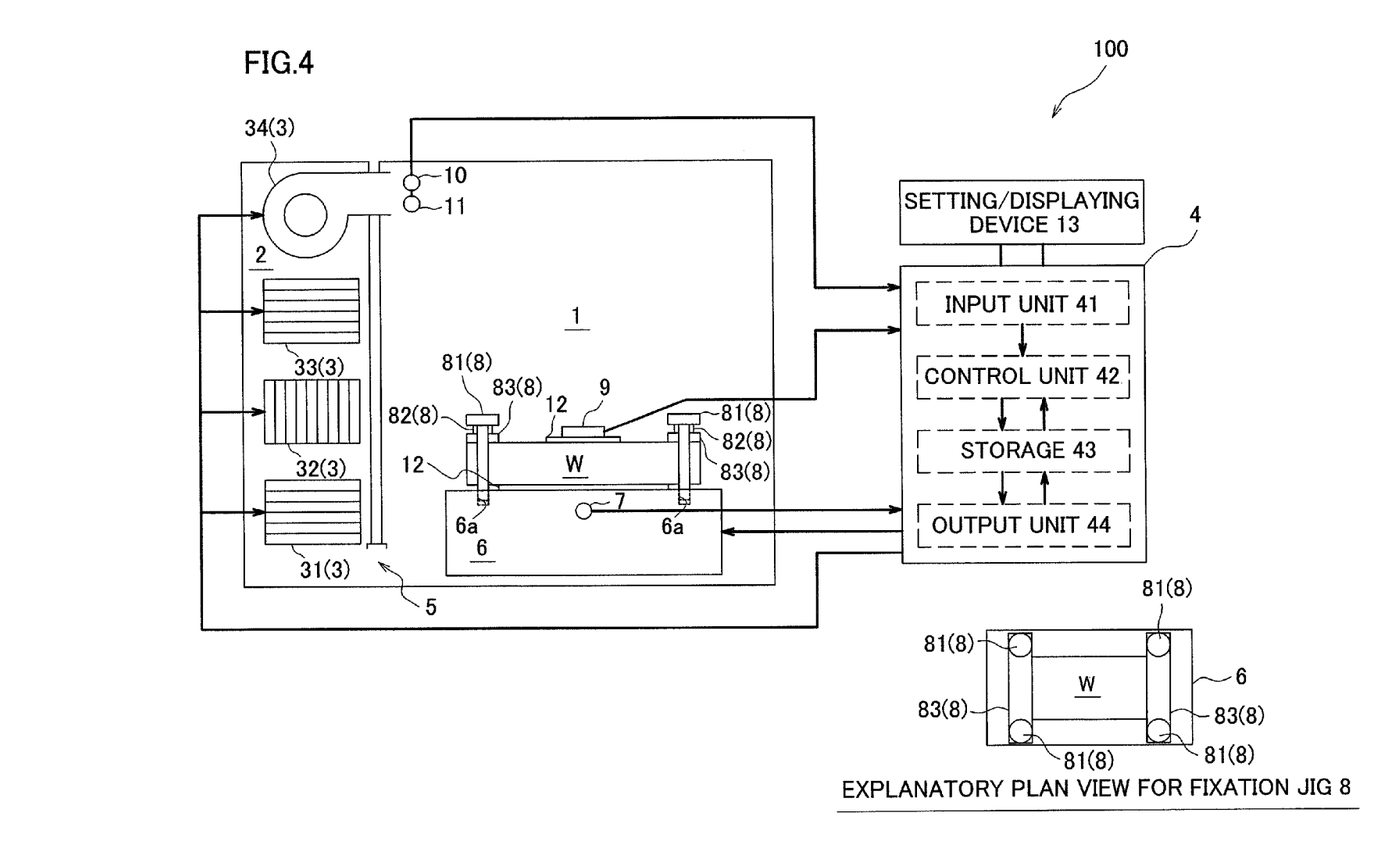
FIG. 4 shows a structure of the environment testing apparatus in which a fixation jig is attached to a cooling/heating plate.

FIG. 4 shows a structure of the environment testing apparatus 100 in which fixation jigs 8 is attached to the cooling/heating plate 6. As shown in FIG. 4, the test object W may be fixed by pressing it against the cooling/heating plate 6 with a use of the fixation jigs 8. Each of the fixation jig 8 includes a screw 81, a spring 82, and a fixing plate 83. On the top surface of the cooling/heating plate 6, there are screw holes 6a for attaching thereto the screws 81, which are provided nearby four corners of the top surface. Each of the screw holes 6a is threaded to form a female screw. Meanwhile, the fixing plate 83 has a hole for inserting therein the screw 81. For example, the fixing plate 83 is a rectangular plate.

On the top surface of the cooling/heating plate 6, the heat transfer sheet 12 is placed and the test object W is placed on the heat transfer sheet 12. The fixing plate 83 is placed on each of two ends of the test object W. Then, with the use of the screw 81 and the spring 82, a predetermined load is applied to the test object W from the top, to fix the test object W to the cooling/heating plate 6. Fixing the test object W to the cooling/heating plate 6 in this way keeps the temperature differential between the cooling/heating plate 6 and the test object W at 0.7° C. or less. In short, the temperatures of the cooling/heating plate 6 and the test object W are made substantially the same.

(Control Method of Environment Testing Apparatus)

Figure 5:
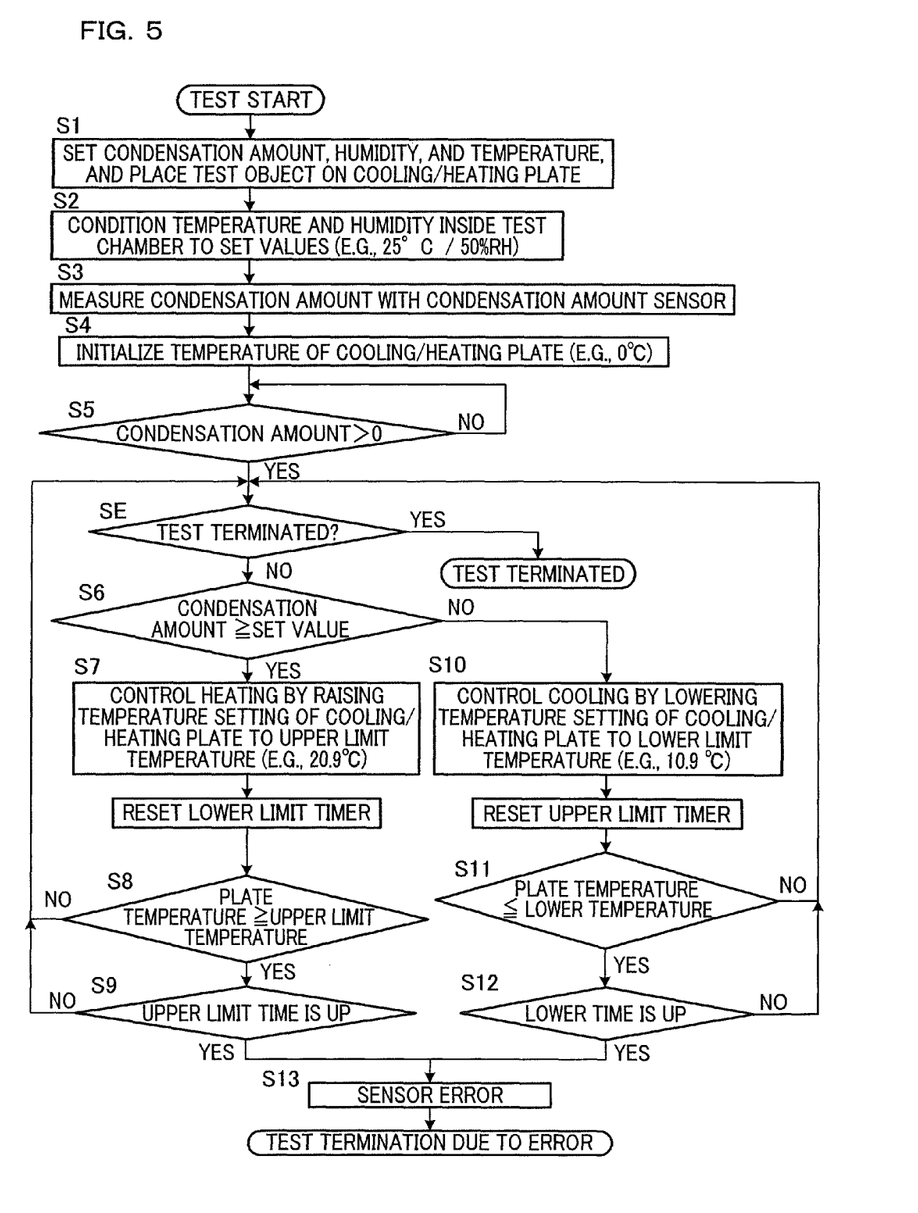
FIG. 5 is a flowchart showing a control method of the environment testing apparatus shown in FIG. 1.

Next, the following describes a control method of the environment testing apparatus 100. FIG. 5 is a flowchart showing the control method of the environment testing apparatus 100 shown in FIG. 1.

(Preparation Process)

A set value of the condensation amount on the surface of the test object W and set values of the temperature and the humidity inside the test chamber 1 are input to the setting/displaying device 13. The test object W is placed on the top surface of the cooling/heating plate 6, with the heat transfer sheet 12 therebetween. This process is shown in FIG. 5 as step 1 (S1; the similar applies to the other steps).

The set value of the condensation amount is a condensation amount ($\mu g/mm^2$) per unit area. Specific examples of the set value are: 3 $\mu g/mm^2$, 5 $\mu g/mm^2$, and 10 $\mu g/mm^2$. Exemplary set values of the temperature and the humidity are 25° C. and 50% RH (where the dew-point temperature is approximately 13.8° C.).

(Constant Temperature Constant Humidity Process)

The heat/humidity generator 3 is operated to condition the air inside the test chamber 1 to predetermined temperature and humidity (e.g. 25° C. and 50% RH) (S2). The regulator 4 receives signals from the dry bulb 10 and the wet bulb 11, via the input unit 41. Based on the received signals, the control unit 42 determines instruction values for the heat/humidity generator 3 (the humidifier 31, the cooler 32, the heater 33, and the air blower 34). The instructions are then output from the output unit 44 to control the heat/humidity generator 3. The air inside the test chamber 1 is circulated by the air blower 34, between the test chamber 1 and the air-conditioning room 2.

When the temperature inside the test chamber 1 is low and the test object W is cold (the temperature of the surface of the test object W is at or lower than the dew-point temperature) due to the winter season or the like, it is preferable to operate the cooling/heating plate 6 (cooling/heating unit) before the constant temperature constant humidity process so as to make the temperature of the surface of the test object W higher than the dew-point temperature corresponding to the set values (warm up process). This is because, in such a case, unexpected condensation occurs on the surface of the test object W when conditioning the air inside the test chamber 1 to the predetermined temperature and humidity (e.g., 25° C. and 50% RH). The dew-point temperature inside the test chamber 1 is derived by the control unit 42 based on the signals from the dry bulb 10 and the wet bulb 11. The temperature of the surface of the test object W may be the temperature obtained by the first temperature sensor 7 or the temperature obtained by the second temperature sensor 91.

(Condensation Amount Measurement Process)

The condensation amount on the surface of the test object W is measured based on signals from the condensation amount sensor 9 (S3). The regulator 4 receives via the input unit 41 signals from the condensation amount sensor 9. Then, based on the signals received from the condensation amount sensor 9, the control unit 42 derives the condensation amount on the surface of the test object W.

The relationship (correlation) between an output (signal) from the condensation amount sensor 9 and the condensation amount ($\mu g/mm^2$) on the surface of the test object W is derived and stored in the storage 43 in advance, as described below. An image of the condensation status of the surface of the test object W is taken by an imaging device such as a microscope. The condensation amount ($\mu g/mm^2$) on the surface of the test object W is derived based on the image having been taken. The correlation between the condensation amount ($\mu g/mm^2$) thus derived and the output (signal) from the condensation amount sensor 9 at this time is input to the storage 43.

(Condensation Amount Control Process)

First, the regulator 4 cools the cooling/heating plate 6 by setting a temperature instruction value for the cooling/heating plate 6 to 0° C., for example (S4). The temperature instruction value for the cooling/heating plate 6 is kept at 0° C. until condensation occurs (S5). This way condensation takes place on the surface of the test object W quickly. That is, the start up period of the condensation test is shortened. Note however that S4 and S5 may be omitted.

Next, based on the condensation amount measured by the condensation amount sensor 9, the regulator 4 controls the cooling/heating plate 6 to approximate the condensation amount on the surface of the test object W to the predetermined amount, by varying the temperature instruction value for the cooling/heating plate 6, within a range between a deviation-added value of a wet bulb temperature obtained by the wet bulb 11, and a deviation-added value of a dew-point temperature of the test chamber 1. For example, the regulator 4 controls the cooling/heating plate 6 so that the condensation amount on the surface of the test object W is the set value ±0.2 $\mu g/mm^2$.

In other words, the regulator 4 sets the upper limit value of the controllable temperature range of the cooling/heating plate 6 to a value proportional to the wet bulb temperature obtained by the wet bulb 11, and sets the lower limit value of the controllable temperature range to a value proportional to the dew-point temperature of the test chamber 1. Then, the temperature instruction value for the cooling/heating plate 6 is varied within the range between the upper limit value and the lower limit value to control the condensation amount on the surface of the test object W. The wet bulb temperature and the dew-point temperature in the test chamber 1 (i.e., temperature and humidity of the test chamber 1) sometimes vary (fluctuate), even if the temperature and the humidity in the test chamber 1 are conditioned through the above S2 to achieve constant temperature and humidity. That is, the deviation-added value of the wet bulb temperature varies proportionally to the wet bulb temperature, when the wet bulb temperature varies. The deviation-added value of the dew-point temperature of the test chamber 1 varies proportionally to the dew-point temperature when the dew-point temperature varies (i.e., the temperature and the humidity vary). The regulator 4 varies the temperature instruction value for the cooling/heating plate 6, to handle the subtle variation in the actual temperature and the humidity inside the test chamber 1. Therefore, even if the temperature and the humidity inside the test chamber 1 fluctuate to some extent, the temperature of the cooling/heating plate 6 is controlled to handle the fluctuation. As the result, it is possible to achieve a stable condensation status on the surface of the test object W, with less variation in the condensation amount. Further, unnecessary temperature increase/decrease of the test object W is prevented.

Further, rapid temperature increase/decrease of the cooling/heating plate 6 is prevented. This not only restrains the unnecessary energy consumption which contributes to energy saving, but also allows a longer life of the relatively less durable cooling/heating plate 6.

Figure 6:
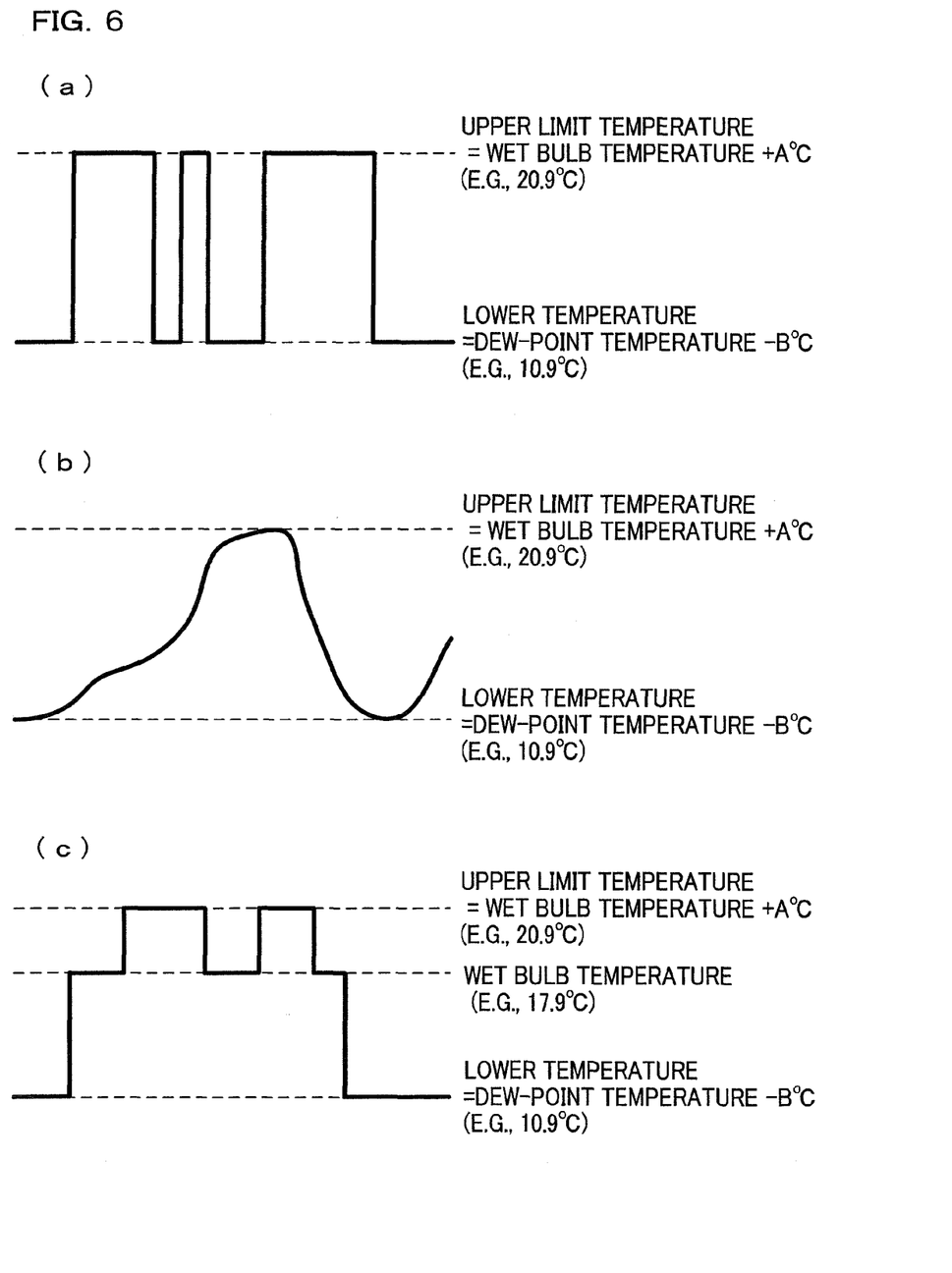
FIG. 6 shows a variation in the temperature instruction value for the cooling/heating plate.

The following elaborates, with reference to FIG. 5 and FIG. 6(a), the control for varying the temperature instruction value for the cooling/heating plate 6, within a range between the deviation-added value of the wet bulb temperature obtained by the wet bulb 11 and the deviation-added value of the dew-point temperature of the test chamber 1, based on the condensation amount measured by the condensation amount sensor 9.

The deviation-added value of the wet bulb temperature obtained by the wet bulb 11 is a value resulting by adding A (deviation) to the wet bulb temperature obtained by the wet bulb 11; i.e. wet bulb temperature +A (° C.). Where the temperature and the humidity inside the test chamber 1 are 25° C. and 50% RH, the wet bulb temperature is 17.9° C., and the value of A (deviation) is 3° C. for example, the deviation-added value of the wet bulb temperature is 20.9° C. as a result of adding 3° C. as A (deviation) to the wet bulb temperature of 17.9° C. As is hereinabove mentioned, if the temperature and the humidity inside the test chamber 1 fluctuate, the wet bulb temperature 17.9° C. varies too. Therefore, the value resulting from adding 3° C. as A (deviation) to the wet bulb temperature also varies proportionally to the wet bulb temperature.

Similarly, the deviation-added value of the dew-point temperature of the test chamber 1 is a value resulting from adding −B (deviation) to the dew-point temperature of the test chamber 1; i.e. the dew-point temperature −B(° C.). When the temperature and the humidity inside the test chamber 1 are 25° C. and 50% RH, the dew-point temperature is 13.9° C., and the value of −B (deviation) is −3° C. for example, the deviation added value of the dew-point temperature is 10.9° C. as a result of adding −3° C. as −B (deviation) to the dew-point temperature of 13.9° C. As is hereinabove mentioned, when the temperature and the humidity inside the test chamber 1 fluctuate, the dew-point temperature 13.9° C. varies too. Therefore, the value resulting from adding −3° C. as −B (deviation) to the dew-point temperature also varies proportionally to the dew-point temperature.

The respective values of A and B (deviations) are determined according to the thermal capacitance, the cooling/heating characteristics, or the like of the test object W, and the values of A and B corresponding to the test object W and the cooling/heating plate 6 are input to the storage 43 in advance.

As shown in FIG. 6(a), based on the condensation amount measured by the condensation amount sensor 9, the regulator 4 switches the temperature instruction value for the cooling/heating plate 6 to one of the following two values: a value resulting from adding, for example, 3° C. (deviation) to the wet bulb temperature obtained by the wet bulb 11 (i.e. upper limit temperature; e.g., 20.9° C.); and a value resulting from adding, for example, −3° C. (deviation) to the dew-point temperature of the test chamber 1 (lower limit temperature; e.g., 10.9° C.). This way, the regulator 4 controls the cooling/heating plate 6 so that the condensation amount on the surface of the test object W is the set value ±0.2 μg/mm².

Note that, in FIG. 6(a), there is no variation in the upper limit temperature (deviation-added value of the wet bulb temperature) or in the lower limit temperature (deviation-added value of the dew-point temperature). However, as is hereinabove mentioned, the upper limit temperature and the lower limit temperature varies in response to variation in the temperature and the humidity inside the test chamber 1. FIG. 6(a) is intended to show that the temperature instruction value for the cooling/heating plate 6 is switched between two levels.

As shown in FIG. 5, the regulator 4 determines whether or not the condensation amount measured by the condensation amount sensor 9 is equal to or more than the set value (S6). If the condensation amount is equal to or higher than the set value, the regulator 4 sets the temperature instruction value for the cooling/heating plate 6 to the upper limit temperature (e.g. 20.9° C.) so as to control heating of the cooling/heating plate 6 (S7). When the condensation amount is less than the set value, the regulator 4 sets the temperature instruction value for the cooling/heating plate 6 to the lower limit temperature (e.g. 10.9° C.) so as to control cooling of the cooling/heating plate 6 (S10).

If the process proceeds to S7, the regulator 4 determines whether the temperature of the cooling/heating plate 6 is equal to or higher than the upper limit temperature (S8). The temperature of the cooling/heating plate 6 is derived from a signal from the first temperature sensor 7. When temperature of the cooling/heating plate 6 is lower than the upper limit temperature, the process returns to S6. When the temperature of the cooling/heating plate 6 is equal to or higher than the upper limit temperature, counting by an upper limit timer is started, and the process returns to S6 on condition that the time is not up (S9). If the time is up, the regulator 4 determines that a sensor error has occurred (S13).

If the process proceeds to S10, the regulator 4 determines whether the temperature of the cooling/heating plate 6 is equal to or lower than the lower limit temperature (S11). If the temperature of the cooling/heating plate 6 is higher than the lower limit temperature, the process returns to S6. If the temperature of the cooling/heating plate 6 is equal to or lower than the lower limit temperature, counting by a lower limit timer is started, and the process returns to S6 on condition that the time is not up (S12). If the time is up, the regulator 4 determines that a sensor error has occurred (S13).

The sensor error is an error taking place in at least one of the condensation amount sensor 9, the first temperature sensor 7, the dry bulb 10, and the wet bulb 11. The error of the condensation amount sensor 9 takes place, for example, when the condensation amount sensor 9 itself breaks down, or when the condensation amount sensor 9 is about to fall off from the heat transfer sheet 12 (or from the test object W). The errors of the first temperature sensor 7 and the dry bulb 10 and the wet bulb 11 take place when these sensors themselves break down.

The following describes a step (SE of FIG. 5) for determining whether the test is to be terminated. Termination of the test is determined based on, for example: (1) whether or not a testing time has elapsed (according to a timer); (2) whether or not a test cycle has completed (according to a program); (3) whether or not a terminating instruction has been manually input; or (4) whether or not an error (including the sensor error) has taken place.

As is shown in S6 to S13 of FIG. 5 and FIG. 6(a), control of the condensation amount on the surface of the test object W is made easy by switching the temperature instruction value for the cooling/heating plate 6 between a value resulted from adding the deviation (A(° C.)) to the wet bulb temperature and a value resulted from adding the deviation (−B(° C.)) to the dew-point temperature; i.e., controlling the condensation amount on the surface of the test object W by switching the temperature instruction value between two levels. In other words, it is a heating period and a cooling period which are controlled, the heating period being a period during which the test object W is heated at a temperature resulting from adding deviation (A(° C.)) to the wet bulb temperature, and the cooling period being a period during which the test object W is cooled at a temperature resulting from adding deviation (−B(° C.)) to the dew-point temperature.

As shown in FIG. 6(b), to approximate the condensation amount on the surface of the test object W to the predetermined amount, it is also preferable to control the cooling/heating plate 6 based on the condensation amount measured by the condensation amount sensor 9, by varying the temperature instruction value for the cooling/heating plate 6 to any given value, instead of several levels, within a range between the deviation-added value of the wet bulb temperature obtained by the wet bulb 11 (upper limit value of the temperature) and the deviation-added value of the dew-point temperature of the test chamber 1 (lower limit value of the temperature). Such a fine control of the temperature instruction value for the cooling/heating plate 6 further restrains variation in the condensation amount.

Further, as shown in FIG. 6(c), it is also preferable to control the condensation amount on the surface of the test object W based on the condensation amount measured by the condensation amount sensor 9, by switching the temperature instruction value for the cooling/heating plate 6 among the deviation-added value of the wet bulb temperature obtained by the wet bulb 11, the value of the wet bulb temperature, and the deviation-added value of the dew-point temperature of the test chamber 1. In other words, the temperature instruction value for the cooling/heating plate 6 is switched among three levels, to control the condensation amount on the surface of the test object W. Thus, there are controlled the heating period during which the test object W is heated at a temperature resulting from adding deviation (A(° C.)) to the wet bulb temperature; a period during which the condensation on the test object W steadily evaporate at the wet bulb temperature; and the cooling period during which the test object W is cooled at a temperature resulting from adding deviation (−B(° C.)) to the dew-point temperature. This further restrains variation in the condensation amount and makes control of the condensation amount easier.

EXAMPLE

Figure 7:
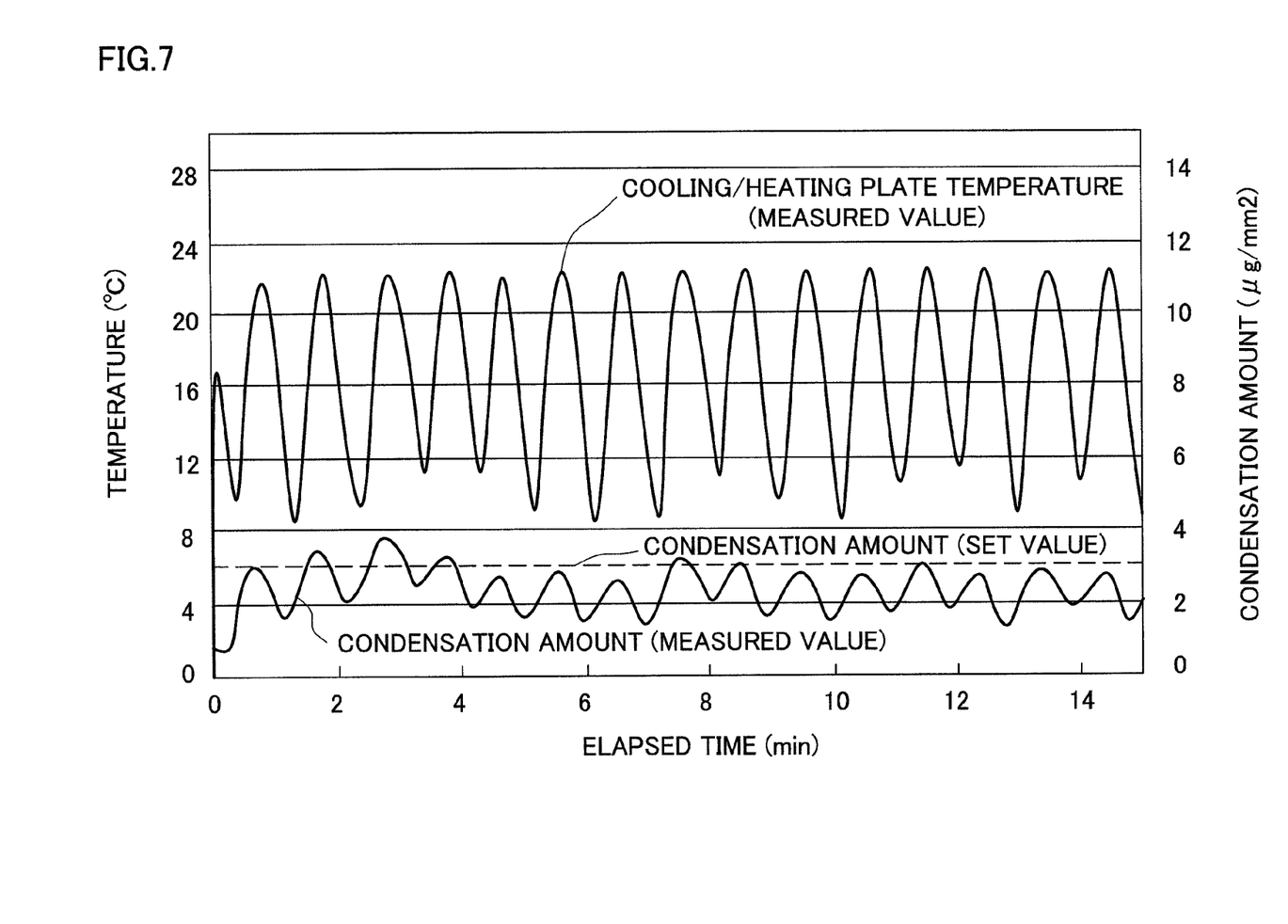
FIG. 7 shows variation in the condensation amount on the surface of a test object and temperature variation of the cooling/heating plate, in cases of using a known-technology.
Figure 8:
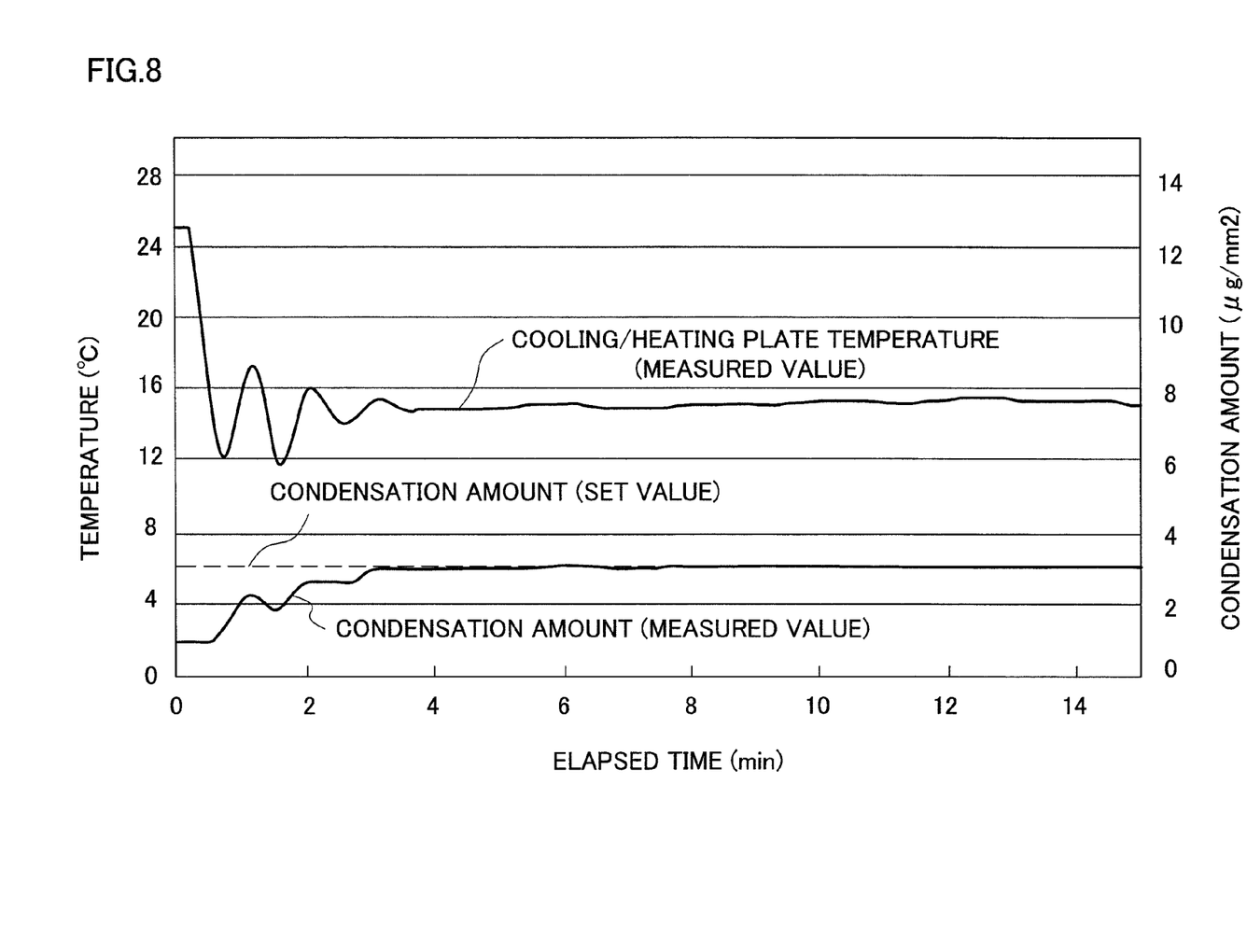
FIG. 8 shows variation in the condensation amount on the surface of a test object and temperature variation in the cooling/heating plate, in cases of using the environment testing apparatus of the embodiment, according to the present invention.

FIG. 7 shows variation in the condensation amount on the surface of a test object and temperature variation of the cooling/heating plate, in cases of using a known-technology. FIG. 8 shows variation in the condensation amount on the surface of a test object W and temperature variation in the cooling/heating plate 6, in cases of using the environment testing apparatus 100 of the embodiment, according to the present invention. For both cases of FIGS. 7 and 8, the condensation test was carried out under common conditions. That is, the set values of the temperature and the humidity inside the test chamber were 25° C. and 50% RH, and the set value for the condensation amount on the surface of each test object was 3 µg/mm².

In the condensation amount control using the known-technology whose result is shown in FIG. 7, the temperature was controlled by using the maximum cooling/heating capability of the cooling/heating plate to approximate the condensation amount to the set value. Specifically, the maximum cooling capability was used to lower the temperature of the cooling/heating plate so as to approximate the condensation amount to 3 µg/mm². Further, the maximum heating capability was used to raise the temperature of the cooling/heating plate to approximate the condensation amount to 3 µg/mm².

On the other hand, in the condensation amount control of the present invention whose result is shown in FIG. 8, a temperature value resulting from adding 3° C. to the wet bulb temperature was set as the upper limit value of the controllable temperature range of the cooling/heating plate 6, and a temperature value resulting from subtracting 3° C. from the dew-point temperature was set as the lower limit value of the controllable temperature range of the cooling/heating plate 6. To approximate the condensation amount to 3 µg/mm², the temperature of the cooling/heating plate was controlled by switching the temperature instruction value for the cooling/heating plate 6 between these two levels; i.e., the upper limit value and the lower limit value. See FIG. 5 for the detailed flow of the control. Note that S4 and S5 shown in FIG. 5 were omitted.

(Test Result)

As shown in FIG. 7, in the condensation amount control using the known-technology, the condensation status of the surface of the test object W was not stable, and the condensation amount varied largely. On the other hand, as shown in FIG. 8, in the condensation amount control of the present invention, the amount of variation in the condensation amount on the surface of the test object W was restrained to a small amount. Compared to the condensation amount control using the known-technology, the amount of variation in the temperature of the cooling/heating plate 6 was also restrained to a small amount.

As hereinabove described, in the condensation amount control of the present invention, the temperature of the cooling/heating plate 6 is controlled by determining the controllable temperature range of the cooling/heating plate 6 based on the temperature and the humidity inside the test chamber 1 obtained from the dry bulb 10 and the wet bulb 11. This enables stable control of the condensation amount, whether the temperature and the humidity inside the test chamber 1 are constant or fluctuating to some extent. Thus, a highly repeatable condensation status is achieved.

An embodiment of the present invention is thus described. It is however obvious to a person with ordinary skill in the art that the present invention is not limited to such an embodiment, and may be altered in various ways within the scope of claims set forth below.

For example, the second temperature sensor 91 may be omitted. Further, the condensation amount sensor 9 does not have to be the one described above, and may be a condensation amount sensor of a different type.

REFERENCE NUMERALS 1 test chamber
2 air-conditioning room
3 heat/humidity generator (air-conditioner)
4 regulator (controller)
6 cooling/heating plate (cooling/heating unit)
9 condensation amount sensor
12 heat transfer sheet
100 environment testing apparatus
W test object

The invention claimed is:

1. An environment testing apparatus, comprising:
a test chamber into which a test object is placed;
a wet bulb and a dry bulb disposed inside the test chamber, which obtain the temperature and the humidity of the air inside the test chamber;
an air-conditioner which conditions the air inside the test chamber to predetermined temperature and humidity, based on signals from the wet bulb and the dry bulb;
a cooling/heating unit accommodated inside the test chamber, which has a top surface for disposing thereon the test object and cools or heats the test object;
a condensation amount sensor to be placed on the test object; and
a controller which controls the condensation amount on the surface of the test object based on signals from the condensation amount sensor, by varying a temperature instruction value for the cooling/heating unit between a deviation-added value of a wet bulb temperature obtained by the wet bulb and a deviation-added value of a dew-point temperature of the test chamber.

2. The environment testing apparatus, according to claim 1, wherein the controller controls the condensation amount on the surface of the test object by switching the temperature instruction value among one of the deviation-added value of the wet bulb temperature, a value of the temperature of the wet bulb, and the deviation-added value of the dew-point temperature.

3. The environment testing apparatus, according to claim 1, wherein the controller controls the condensation amount on the surface of the test object by switching the temperature instruction value between the deviation-added value of the wet bulb temperature and the deviation-added value of the dew-point temperature.

4. A method of controlling an environment testing apparatus including:
- a test chamber into which a test object is placed;
- a wet bulb and a dry bulb disposed inside the test chamber, which obtain the temperature and the humidity of the air inside the test chamber;
- an air-conditioner which conditions the air inside the test chamber to predetermined temperature and humidity, based on signals from the wet bulb and the dry bulb;
- a cooling/heating unit accommodated inside the test chamber, which has a top surface for disposing thereon the test object and cools or heats the test object; and
- a condensation amount sensor to be placed on the test object, the method comprising the steps of:
- conditioning the air inside the test chamber to predetermined temperature and humidity by operating the air-conditioner;
- measuring a condensation amount on the surface of the test object based on signals from the condensation amount sensor; and
- controlling the condensation amount on the surface of the test object so as to approximate the condensation amount to a predetermined amount, based on the condensation amount thus measured, by varying a temperature instruction value for the cooling/heating unit between a deviation-added value of a wet bulb temperature obtained by the wet bulb and a deviation-added value of a dew-point temperature of the test chamber.

* * * * *